US011426005B2

(12) United States Patent
Fukuyama et al.

(10) Patent No.: US 11,426,005 B2
(45) Date of Patent: Aug. 30, 2022

(54) SLEEP APPARATUS (71) Applicant: TOYOTA JIDOSHA KABUSHIKI KAISHA, Aichi-ken (JP)

(72) Inventors: Gen Fukuyama, Nagoya (JP); Mikio Inoue, Nagoya (JP); Masaya Osaka, Nagoya (JP); Shugen Yamamura, Nagoya (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 0 days.

(21) Appl. No.: 17/159,148

(22) Filed: Jan. 27, 2021

(65) Prior Publication Data
US 2021/0259428 A1 Aug. 26, 2021

(30) Foreign Application Priority Data

Feb. 21, 2020 (JP) .............................. JP2020-028738

(51) Int. Cl.
A47C 17/00 (2006.01)
A47C 17/16 (2006.01)
A47C 17/17 (2006.01)
A47C 17/213 (2006.01)
A47C 27/10 (2006.01)

(52) U.S. Cl.
CPC ........... A47C 17/163 (2013.01); A47C 17/17 (2013.01); A47C 17/213 (2013.01); A47C 27/10 (2013.01)

(58) Field of Classification Search
CPC ....... A47C 17/00; A47C 17/04; A47C 17/163; A47C 17/17; A47C 17/213; A47C 27/10; A61G 7/05769; A61G 7/001; A61B 5/447
See application file for complete search history.

(56) References Cited

U.S. PATENT DOCUMENTS

| 2004/0103475 | A1  | 6/2004  | Ogawa et al.      |              |
|--------------|-----|---------|-------------------|--------------|
| 2012/0291204 | A1  | 11/2012 | Takeda et al.     |              |
| 2014/0304915 | A1  | 10/2014 | Lachenbruch       |              |
| 2014/0345060 | A1* | 11/2014 | Ribble            | A61B 5/4818  |
|              |     |         |                   | 5/706        |
| 2016/0008198 | A1  | 1/2016  | Takeda et al.     |              |
| 2016/0120716 | A1* | 5/2016  | Ribble            | A61G 13/08   |
|              |     |         |                   | 5/616        |
| 2016/0324707 | A1  | 11/2016 | Lachenbruch et al.|              |
| 2017/0015423 | A1* | 1/2017  | Udriste           | B60N 2/34    |

FOREIGN PATENT DOCUMENTS

| EP | 2484327 A2    | 8/2012  |
|----|---------------|---------|
| JP | S63222711 A   | 9/1988  |
| JP | 200424678 A   | 1/2004  |
| JP | 2004121837 A  | 4/2004  |
| JP | 2011160892 A  | 8/2011  |
| WO | 02051287 A2   | 7/2002  |
| WO | 2006136854 A1 | 12/2006 |
| WO | 2013177338 A2 | 11/2013 |

* cited by examiner

Primary Examiner — Fredrick C Conley
(74) Attorney, Agent, or Firm — Hauptman Ham, LLP (57) ABSTRACT A sleep apparatus includes: a mat main body portion configured to support a user in a supine state; and a tilting mechanism that, at the mat main body portion, periodically tilts a body of a user left and right, by alternately raising a right side supporting portion, which includes portions supporting a right-side hipbone and a right-side shoulder blade of a user, and a left side supporting portion, which includes portions supporting a left-side hipbone and a left-side shoulder blade of a user.

12 Claims, 10 Drawing Sheets

SLEEP APPARATUS

CROSS-REFERENCE TO RELATED APPLICATION

This application is based on and claims priority under 35 USC 119 from Japanese Patent Application No. 2020-028738, filed on Feb. 21, 2020, the disclosure of which is incorporated by reference herein.

BACKGROUND

Technical Field

The present disclosure relates to a sleep apparatus.

Related Art

Japanese Patent Application Laid-Open (JP-A) No. 2004-024678 discloses a device in which a vibrating plate is provided at a bed, and that provides a sleep inducing effect to a person who is lying-down on the bed by applying continuous minute vibrations and vibrations that repeat at a given cycle to the vibrating plate.

However, the device disclosed in JP-A No. 2004-024678 does not consider maintaining a favorable sleeping state. In particular, in a case in which the user is sleeping on a bed with a narrow width, or the like, rolling-over while sleeping is difficult, and therefore, there is room for improvement.

SUMMARY

The present disclosure provides a sleep apparatus that may maintain a favorable sleeping state even in a case in which the width of the sleeping space is narrow.

A first aspect of the present disclosure is a sleep apparatus including: a mat main body portion configured to support a user in a supine state; and a tilting mechanism that, at the mat main body portion, periodically tilts a body of a user left and right, by alternately raising a right side supporting portion, which includes portions supporting a right-side hipbone and a right-side shoulder blade of a user, and a left side supporting portion, which includes portions supporting a left-side hipbone and a left-side shoulder blade of a user.

In the first aspect of the present disclosure, the mat main body portion configured to support the user in a supine state. Further, the right side supporting portion, which includes portions that support the right-side hipbone and the right-side shoulder blade of the user, and the left side supporting portion, which includes portions that support the left-side hipbone and the left-side shoulder blade of the user, are provided at the mat main body portion. The body of the user is tilted left and right periodically due to the tilting mechanism alternately raising the right side supporting portion and the left side supporting portion. By tilting the body of the user left and right periodically in this way, the regions to which body pressure is applied may be changed periodically.

By the way, it is known that, while a person is sleeping, the person rolls over in their sleep several tens of times for the purpose of promoting blood circulation and the like. Here, in the sleep apparatus relating to the first aspect, circulation of blood is promoted due to the regions, to which body pressure is applied, of the user being changed periodically by the tilting mechanism, and therefore, the sleeping state may be maintained favorable without the user rolling-over in their sleep.

In a second aspect of the present disclosure, in the above first aspect, the mat main body portion may include a central supporting portion configured to support buttocks and thigh regions of a user, an upper side supporting portion that is rotatably connected to one end side of the central supporting portion and configured to support a back region and head portion of a user, and a lower side supporting portion that is rotatably connected to another end side of the central supporting portion and configured to support leg portions of a user, and the mat main body portion may be configured to alternately switch between a seat state and a bed state, by the upper side supporting portion and the lower side supporting portion rotating with respect to the central supporting portion.

In the second aspect of the present disclosure, the mat main body portion is configured to alternately switch between a seat state and a bed state. Therefore, when a user is seated on the mat main body portion that is in the seat state, the buttocks and thigh regions of the user are supported from the lower side by the central supporting portion, and the back region and head portion are supported from the rear side by the upper side supporting portion, and the leg portions are supported from the rear side by the lower side supporting portion. Due to the mat main body portion being switched-over from this seating state to the bed state, the user may assume a recumbent posture without separating from the mat main body.

In a third aspect if the present disclosure, in the above second aspect, a pair of left and right head portion restraining cushions may be provide at the upper side supporting portion such that a head portion of a user is located therebetween.

A fourth aspect of the present disclosure, in the second aspect or the third aspect, may further include: a plurality of supporting airbags provided at the mat main body portion, wherein: internal air pressures of the supporting airbags are respectively adjustable, the supporting airbags are disposed along a direction heading from the upper side supporting portion toward the lower side supporting portion, and the internal air pressures of the supporting airbags are adjusted such that the internal air pressures of the supporting airbags at the central supporting portion are higher in the bed state than in the seat state.

In the fourth aspect of the present disclosure, the plural supporting airbags are disposed along the direction heading from the upper side supporting portion toward the lower side supporting portion of the mat main body portion. The respective supporting airbags are structured such that the air pressures of the interiors thereof may be changed. Due thereto, the hardness of the mat main body portion may be adjusted in accordance with the posture of the user.

Further, the air pressures of the supporting airbags are adjusted such that the air pressures of the supporting airbags that are at the central supporting portion are higher in the bed state than in the seat state. Due thereto, in the bed state, the air pressures of the supporting airbags at the central supporting portion may be raised, and it may be made easy to tilt the body of the user to the left and the right, while, in the seat state, the air pressures of the supporting airbags at the central supporting portion may be lowered, and the buttocks and thigh regions of the user may be supported so as to be enfolded.

A fifth aspect of the present disclosure, in any one of the second aspect to the fourth aspect, may further include: a wakefulness sensor, which senses a degree of wakefulness of a user seated on the mat main body portion in the seat state, wherein, in a case in which the degree of wakefulness of a user that is sensed by the wakefulness sensor is lower than a predetermined value, the mat main body portion is switched from the seat state to the bed state.

In the fifth aspect of the present disclosure, the mat main body portion is switched from the seat state to the bed state in a case in which the awakeness degree of the user is lower than a predetermined value, such as, for example, when the user falls asleep or the like. Due thereto, in a case in which the user falls asleep in a state of being seated on the mat main body portion that is in the seat state, the user may be switched-over to a recumbent posture without waking the user.

In a sixth aspect of the present disclosure, in the fifth aspect, the wakefulness sensor comprises a body pressure sensor that is provided at a position of the mat main body portion corresponding to a heart of a user, and that is configured to sense a heartbeat of a user.

A seventh aspect of the present disclosure, in any one of the first aspect to the sixth aspect, may further include: a depth sensor that senses a depth of sleep of a user, wherein, in a case in which a depth of sleep of a user that is sensed by the depth sensor is deeper than a predetermined value in the bed state, the tilting mechanism alternately raises the right side supporting portion and the left side supporting portion.

In the seventh aspect of the present disclosure, in a case in which the depth of sleep of the user that is sensed by the depth sensor is deeper than a predetermined value, the user is tilted left and right due to the right side supporting portion and the left side supporting portion being raised alternately. Due thereto, the user may be tilted left and right without the user, who is sleeping, noticing. Note that what is called here a case in which the depth of sleep is deep is, for example, a depth of sleep of 2 or 3, which is a deep sleep, among the three levels of depth of non-REM sleep.

An eighth aspect of the present disclosure, in any one of the second aspect to the seventh aspect, may further include: armrests that are provided at respective side portions of the mat main body portion, and that are configured to support arms of a user in the seat state; and armrest mechanisms that, at a time of switching from the seat state to the bed state, are configured to lower the armrests in conjunction with rotation of the upper side supporting portion.

In the eighth aspect of the present disclosure, armrests are provided at respective side portions of the mat main body portion. Further, at the time of switching from the seat state to the bed state, the armrest movement mechanisms lower the armrests in conjunction with the rotation of the upper side supporting portion. Due thereto, the user may be switched to a recumbent posture naturally even in a case in which the user falls asleep with his/her arms resting on the armrests in the state in which the user is seated on the mat main body portion that is in the seat state.

In a ninth aspect of the present disclosure, in any one of the first aspect to the eighth aspect, the tilting mechanism may comprise: tilting airbags that are provided at the right side supporting portion and the left side supporting portion, respectively; and an air supply portion that supplies air to the tilting airbags.

In the ninth aspect of the present disclosure, due to air being supplied from the air supply portion, the tilting airbags of the right side supporting portion and the tilting airbags of the left side supporting portion may be inflated alternately.

In a tenth aspect of the present disclosure, in any one of the first aspect to the eighth aspect, the tilting mechanism may comprise a tilting device that tilts the entire mat main body portion left and right.

In the tenth aspect of the present disclosure, the body of the user may be tilted left and right due to the entire mat main body portion being tilted left and right.

In a eleventh aspect of present disclosure, in any one of the first aspect to the tenth aspect, the sleep apparatus may be disposed within a passenger cabin of a vehicle.

In accordance with the sleep apparatus relating to the present disclosure, the sleeping state may be maintained favorable even in a case in which the width of the sleeping space is narrow.

Further, in accordance with the sleep apparatus relating to the present disclosure, the sleep apparatus may be used both with the user in a seated posture and with the user in a recumbent posture.

In accordance with the sleep apparatus relating to the present disclosure, the comfort of the user may be ensured in both the seat state and the bed state.

Further, in accordance with the sleep apparatus relating to the present disclosure, the comfort of the user may be improved.

Moreover, in accordance with the sleep apparatus relating to the present disclosure, the sleeping state may be maintained favorable without disturbing the sleep of the user.

Further, in accordance with the sleep apparatus relating to the present disclosure, disturbing of the sleep of the user at the time when the user switches to a recumbent posture may be suppressed, as compared with in a structure that does not have the armrest moving mechanisms.

Moreover, in accordance with the sleep apparatus relating to the present disclosure, the body of the user may be tilted left and right by a simple structure.

In accordance with the sleep apparatus relating to the present disclosure, the body of the user may be tilted left and right rapidly, as compared with in a structure in which airbags are inflated, and the right side supporting portion and the left side supporting portion are raised.

BRIEF DESCRIPTION OF THE DRAWINGS

Exemplary embodiments of the present disclosure will be described in detail based on the following figures, wherein.

DETAILED DESCRIPTION

A sleep apparatus 10 relating to a first embodiment is described with reference to the drawings. Note that arrow FR, arrow UP and arrow RH that are illustrated appropriately in the respective drawings indicate the seat forward direction, the seat upper side and the right side in the seat width direction, respectively, of the sleep apparatus 10. Hereinafter, when description is given by merely using front-rear, vertical, and left-right directions, they refer to the front and rear of the seat front-rear direction, up and down in the seat vertical direction, and the left and right in the seat width direction, unless otherwise specified.

Figure 1:
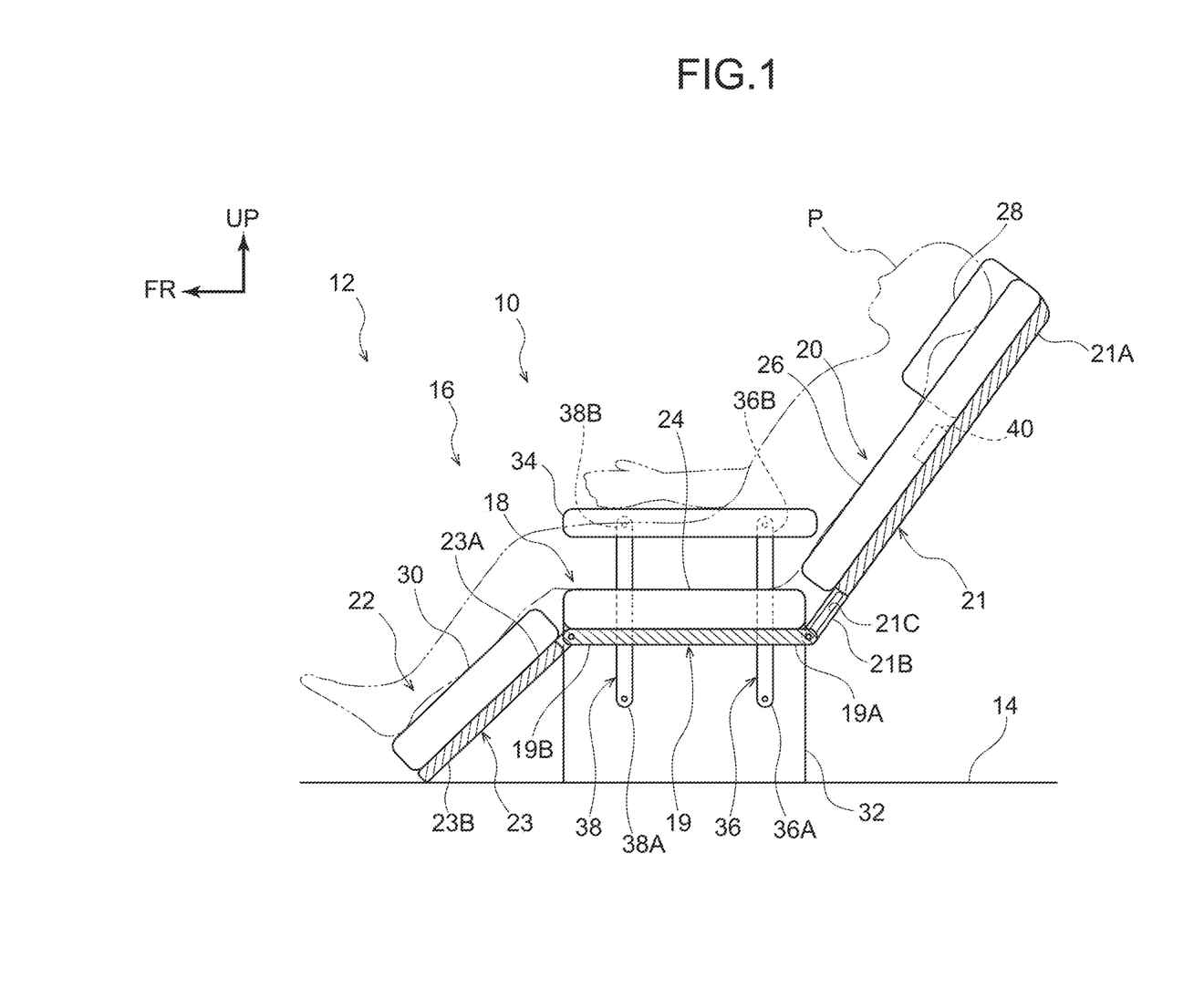
FIG. 1 is a schematic side sectional view in which an sleep apparatus relating to a first embodiment is seen from a seat width direction, and is a drawing illustrating a seat state.

As illustrated in FIG. 1, the sleep apparatus 10 of the present embodiment is disposed within the passenger cabin of a vehicle 12. In the present embodiment, as an example, in the state in which a user P is seated on the sleep apparatus 10, the direction in which the user P faces coincides with the vehicle forward direction, and the left-right direction of the user P coincides with the left-right direction that is the transverse direction of the vehicle.

The sleep apparatus 10 of the present embodiment has a mat main body portion 16. This mat main body portion 16 is structured so as to be able to switch-over alternately between the seat state illustrated in FIG. 1 and the bed state illustrated in FIG. 2. In the seat state, the user P may sit on the mat main body portion 16, and in the bed state, the user P may be supported by the mat main body portion 16 in a supine state.

As illustrated in FIG. 1, the mat main body portion 16 is structured to include a central supporting portion 18, an upper side supporting portion 20 and a lower side supporting portion 22. The central supporting portion 18 is mounted to a pair of left and right side frames 32 that stand upright at a floor panel 14, and is structured so as to be able to support the buttocks and the thigh regions of the user P. Note that, in FIG. 1, only the side frame 32 that is at the right side is illustrated.

Figure 5:
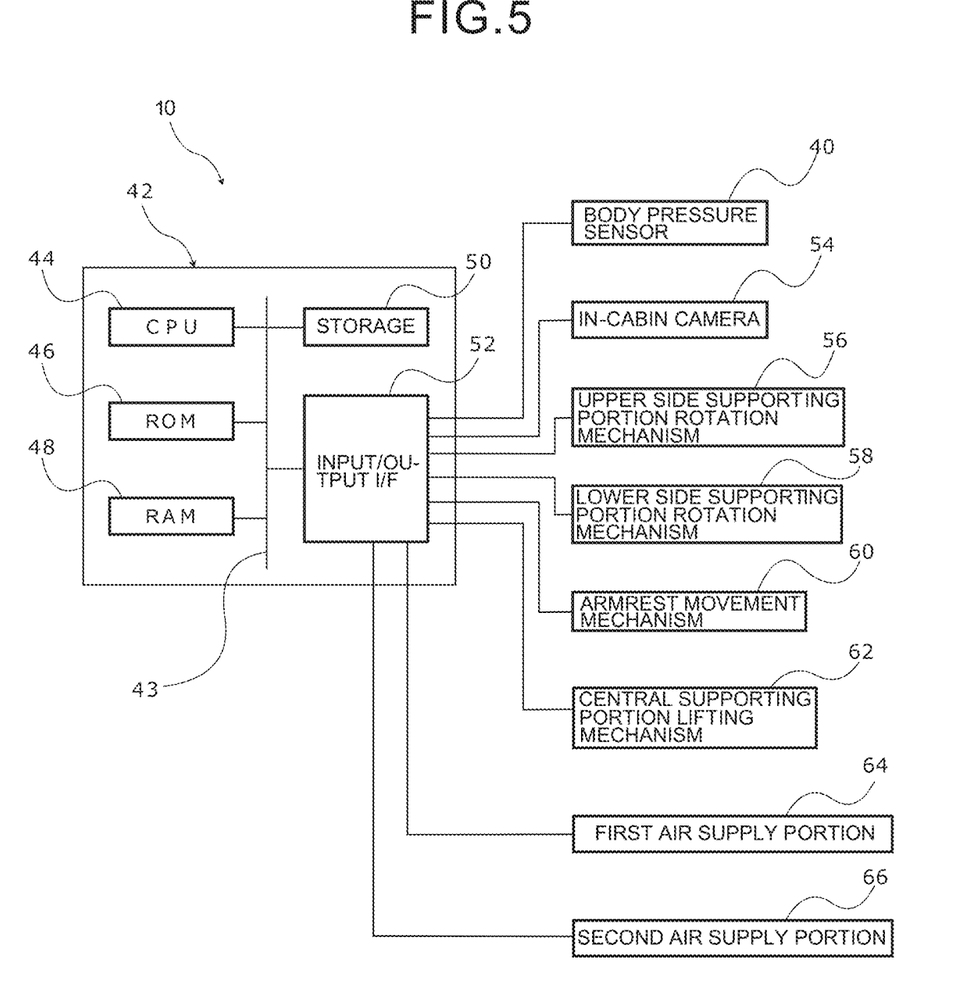
FIG. 5 is a block drawing illustrating hardware configuration of the sleep apparatus relating to the first embodiment.

The central supporting portion 18 has a central supporting frame 19, and a central cushion 24 is mounted on this central supporting frame 19. The buttocks and the thigh regions of the user are supported from the seat lower side by the central cushion 24. Namely, the central supporting portion 18 functions as a seat cushion of a general vehicle seat. Further, the seat width direction both end portions of the central supporting frame 19 are mounted to the side frames 32 so as to be able to be raised and lowered. Moreover, a central supporting portion lifting mechanism 62 illustrated in FIG. 5 is provided at the interior of the side frame 32. The central supporting portion 18 may be raised and lowered alternately between the position illustrated in FIG. 1 and the position illustrated in FIG. 2 due to this central supporting portion lifting mechanism 62 operating.

As illustrated in FIG. 1, the upper side supporting portion 20 is rotatably connected to a rear end portion 19A of the central supporting frame 19. This upper side supporting portion 20 is structured so as to be able to support the back region and the head portion of the user P. Concretely, the upper side supporting portion 20 has an upper side supporting frame 21. A lower end portion 21B of this upper side supporting frame 21 is rotatably connected to the central supporting frame 19.

Figure 3:
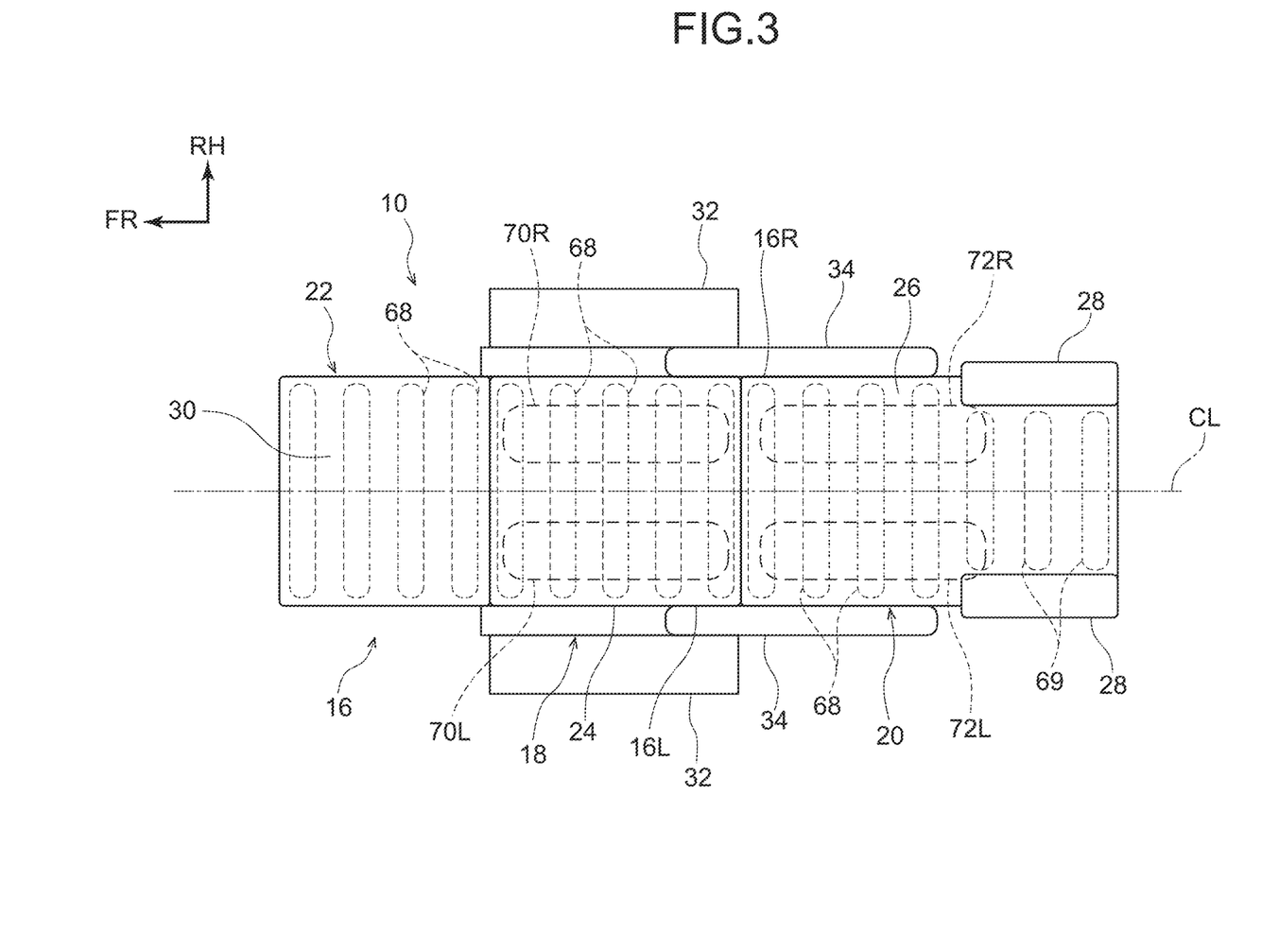
FIG. 3 is a schematic plan view in which the sleep apparatus relating to the first embodiment is seen from the seat upper side.

An upper side cushion 26 is mounted on the upper side supporting frame 21. The back region and the head portion of the user P are supported from the seat rear side by this upper side cushion 26. Namely, the upper side supporting portion 20 functions as the seatback of a general vehicle seat. Further, a body pressure sensor 40 that serves as an awakeness degree sensor is provided at the interior of the upper side cushion 26. The body pressure sensor 40 is provided at a position of the upper side seat cushion 26 which position corresponds to the heart of the user P, and the heartbeat of the user P may be sensed by the body pressure sensor 40. Moreover, head portion restraining cushions 28 are provided at an upper end portion 21A side of the upper side supporting frame 21 at the upper side cushion 26. As illustrated in FIG. 3, the pair of head portion restraining cushions 28 are provided at the left and right such that the head portion of the user P is located therebetween, and are cushions for keeping the head portion of the user P from falling toward the outer sides of the upper side supporting portion 20.

As illustrated in FIG. 1, in the present embodiment, as an example, a guide hole 21C is formed in the lower end portion 21B of the upper side supporting frame 21. Therefore, due to the upper side supporting frame 21 being slid along this guide hole 21C, the central cushion 24 and the upper side cushion 26 are made to approach or move away from one another. In the seat state illustrated in FIG. 1, the upper side supporting frame 21 may be rotated with respect to the central supporting frame 19 due to the central cushion 24 and the upper side cushion 26 being moved away from one another. On the other hand, in the bed state illustrated in FIG. 2, the gap between the central cushion 24 and the upper side cushion 26 is eliminated due to the central cushion 24 and the upper side cushion 26 being made to approach one another.

As illustrated in FIG. 1, the lower side supporting portion 22 is rotatably connected to a front end portion 19B of the central supporting frame 19, and this lower side supporting portion 22 is structured so as to be able to support the leg portions of the user P. Concretely, the lower side supporting portion 22 has a lower side supporting frame 23. An upper end portion 23A of this lower side supporting frame 23 is rotatably connected to the central supporting frame 19. Further, a lower end portion 23B of the lower side supporting frame 23 abuts or is near to the floor panel 14.

A lower side cushion 30 is mounted on the lower side supporting frame 23. The leg portions of the user P are supported from the seat rear side by the lower side cushion 30. The lower side cushion 30 is provided at a position of being disposed such that, in the bed state, there is no gap between the lower side cushion 30 and the central cushion 24.

The mat main body portion 16 is structured as described above. As illustrated in FIG. 3, the portion that is further toward the right side than a central line CL, which extends in the seat front-rear direction through the seat width direction center at the mat main body portion 16, is called a right side supporting portion 16R. Further, the portion that is further toward the left side than the central line CL is called a left side supporting portion 16L. The right side supporting portion 16R is a region that includes portions that support the right-side hipbone and the right-side shoulder blade of the user P. The left side supporting portion 16L is a region that includes portions that support the left-side hipbone and the left-side shoulder blade of the user P.

Armrests 34, which may support the arms of the user P in the seat state, are provided at both side portions of the mat main body portion 16. As illustrated in FIG. 1, in the seat state, the armrests 34 are disposed above the side frames 32, and extend in the seat front-rear direction. Further, the armrests 34 are connected to the side frames 32 by first links 36 and second links 38.

The first link 36 is formed in an elongated shape, and one end portion 36A of the first link 36 is rotatably mounted to the side frame 32. Another end portion 36B of the first link 36 is rotatably mounted to a rear portion of the armrest 34.

The second link 38 is provided further toward the seat front side than the first link 36, and has the same shape as the first link 36. One end portion 38A of the second link 38 is rotatably mounted to the side frame 32. Another end portion 38B of the second link 38 is rotatably mounted to the front portion of the armrest 34.

The armrest 34 is structured as described above. Rotation of the first link 36 and the second link 38 is locked by an unillustrated locking mechanism such that the first link 36 and the second link 38 do not rotate inadvertently in the state of usual usage. Further, armrest movement mechanisms 60 illustrated in FIG. 5 are provided at the interiors of the side frames 32. Due to the armrest movement mechanisms 60 operating at the time when the mat main body portion 16 switches-over from the seat state to the bed state, the locked states of the first links 36 and the second links 38 are cancelled. Then, in conjunction with the rotation of the upper side supporting portion 20, the armrest movement mechanisms 60 lower the armrests 34 while moving the armrests 34 toward the seat rear side. Further, conversely, due to the armrest movement mechanisms 60 operating at the time when the mat main body portion 16 switches-over from the bed state to the seat state, the locked states of the first links 36 and the second links 38 are cancelled, and thereafter, in conjunction with the rotation of the upper side supporting portion 20, the armrest movement mechanisms 60 raise the armrests 34 while moving the armrests 34 toward the seat front side.

Here, as illustrated in FIG. 3, supporting bladders 68, which serve as plural supporting airbags, are disposed at the mat main body portion 16 along the direction heading from the upper side supporting portion 20 toward the lower side supporting portion 22. Concretely, the supporting bladders 68 are formed in shapes of elongated bags whose length directions are the seat width direction. The supporting bladders 68 are disposed between the central cushion 24 and the central supporting frame 19, and between the upper side cushion 26 and the upper side supporting frame 21, and between the lower side cushion 30 and the lower side supporting frame 23, respectively. Note that, in FIG. 3, five of the supporting bladders 68 are illustrated between the central cushion 24 and the central supporting frame 19, but, in actuality, even more of the supporting bladders 68 are arrayed in the seat front-rear direction.

At the upper side supporting portion 20, supporting bladders 69, whose lengths in the seat width direction are shorter than those of the supporting bladders 68, are disposed at the portion that supports the head portion of the user P. These supporting bladders 68 and supporting bladders 69 are structured such that the internal air pressures thereof may be changed. Concretely, air is supplied to the supporting bladders 68 and the supporting bladders 69 from a first air supply portion 64 that is illustrated in FIG. 5, and the amount of air that is supplied to the supporting bladders 68 and the supporting bladders 69 from the first air supply portion 64 may be adjusted. Therefore, a portion of the mat main body portion 16 may be made to be hard by making the air pressures of some of the supporting bladders 68 be higher than those of others of the supporting bladders 68. Similarly, a portion of the mat main body portion 16 may be made to be soft by making the air pressures of some of the supporting bladders 68 lower than those of others of the supporting bladders 68.

A right side bladder 70R and a left side bladder 70L that serve as tilting airbags are provided at the central supporting portion 18. The right side bladder 70R and the left side bladder 70L are provided between the central cushion 24 and the central supporting frame 19, and are formed in shapes of bags whose length directions are the seat front-rear direction. The right side bladder 70R is disposed at the right side supporting portion 16R that includes a portion that supports the periphery of the right-side hipbone of the user P. The left side bladder 70L is disposed at the left side supporting portion 16L that includes a portion that supports the periphery of the left-side hipbone of the user P. Note that the positions of the hipbones are different in a case in which the user P has a large physique and in a case in which the user P has a small physique, but the right side bladder 70R and the left side bladder 70L are formed in shapes that may support the hipbones from the seat lower side in both cases.

A right side bladder 72R and a left side bladder 72L that serve as tilting airbags are provided at the upper side supporting portion 20. The right side bladder 72R and the left side bladder 72L are provided between the upper side cushion 26 and the upper side supporting frame 21, and are formed in shapes of bags whose length directions are the seat front-rear direction. The right side bladder 72R is disposed at the right side supporting portion 16R that includes a portion that supports the periphery of the right-side shoulder blade of the user P. The left side bladder 72L is disposed at the left side supporting portion 16L that includes a portion that supports the periphery of the left-side shoulder blade of the user P. Note that the positions of the shoulder blades are different in a case in which the user P has a large physique and in a case in which the user P has a small physique, but the right side bladder 72R and the left side bladder 72L are formed in shapes that may support the shoulder blades from the seat lower side in both cases.

The right side bladder 70R, the right side bladder 72R, the left side bladder 70L and the left side bladder 72L are structured so as to be able to inflate due to air being supplied thereto from a second air supply portion 66 that is illustrated in FIG. 5. Further, the tilting mechanism is structured to include the right side bladder 70R, the right side bladder 72R, the left side bladder 70L, the left side bladder 72L, and the second air supply portion 66.

FIG. 5 is a block drawing illustrating hardware configuration of the sleep apparatus 10. As illustrated in FIG. 5, the sleep apparatus 10 has a control section 42. This control section 42 is configured to include a CPU (Central Processing Unit: processor) 44, a ROM (Read Only Memory) 46, a RAM (Random Access Memory) 48, a storage 50 and an input/output interface 52. These respective configurations are connected so as to be able to communicate with one another via a bus 43.

The CPU 44 is a central computing processing unit, and executes various programs and controls respective sections. Namely, the CPU 44 reads-out a program from the ROM 46 or the storage 50, and executes the program by using the RAM 48 as a workspace. The CPU 44 carries out control of the above-described respective configuration and various types of computing processings in accordance with programs that are recorded in the ROM 46 or the storage 50.

The ROM 46 stores various programs and various data. The RAM 48 temporarily storage programs and data as a workspace. The storage 50 is configured by an HDD (Hard Disk Drive) or an SSD (Solid State Drive), and is a non-transitory recording medium that stores various programs, including the operating system, and various data. In the present embodiment, a program for carrying out bladder controlling processing, and various data and the like are stored in the ROM 46 or the storage 50.

The input/output interface 52 is electrically connected to the body pressure sensor 40, an in-cabin camera 54 that serves as an awakeness degree sensor, an upper side supporting portion rotation mechanism 56, a lower side supporting portion rotation mechanism 58, the armrest movement mechanisms 60, the central supporting portion lifting mechanism 62, the first air supply portion 64 and the second air supply portion 66. The body pressure sensor 40 senses changes in pressure due to the heartbeat of the user P, and transmits data to the control section 42.

The in-cabin camera 54 is provided within the passenger cabin, and faces the user P who is in a state of being seated on the sleep apparatus 10. As an example, the present embodiment is configured such that the face of the user P is imaged by the in-cabin camera 54, and the captured data is transmitted to the control section 42.

The upper side supporting portion rotation mechanism 56 is a mechanism that rotates the upper side supporting portion 20 with respect to the central supporting portion 18. Concretely, the upper side supporting portion rotation mechanism 56 is structured to include an unillustrated motor that is provided at the connected portion of the central supporting frame 19 and the upper side supporting frame 21. Due to this motor being operated, the upper side supporting frame 21 is rotated with respect to the central supporting frame 19.

The lower side supporting portion rotation mechanism 58 is a mechanism that rotates the lower side supporting portion 22 with respect to the central supporting portion 18. Concretely, the lower side supporting portion rotation mechanism 58 is structured to include an unillustrated motor that is provided at the connected portion of the central supporting frame 19 and the lower side supporting frame 23. Due to this motor being operated, the lower side supporting frame 23 is rotated with respect to the central supporting frame 19.

The sleep apparatus 10 realizes various functions by using the above-described hardware resources. The functional configurations that are realized by the sleep apparatus 10 are described with reference to FIG. 7.

Figure 7:
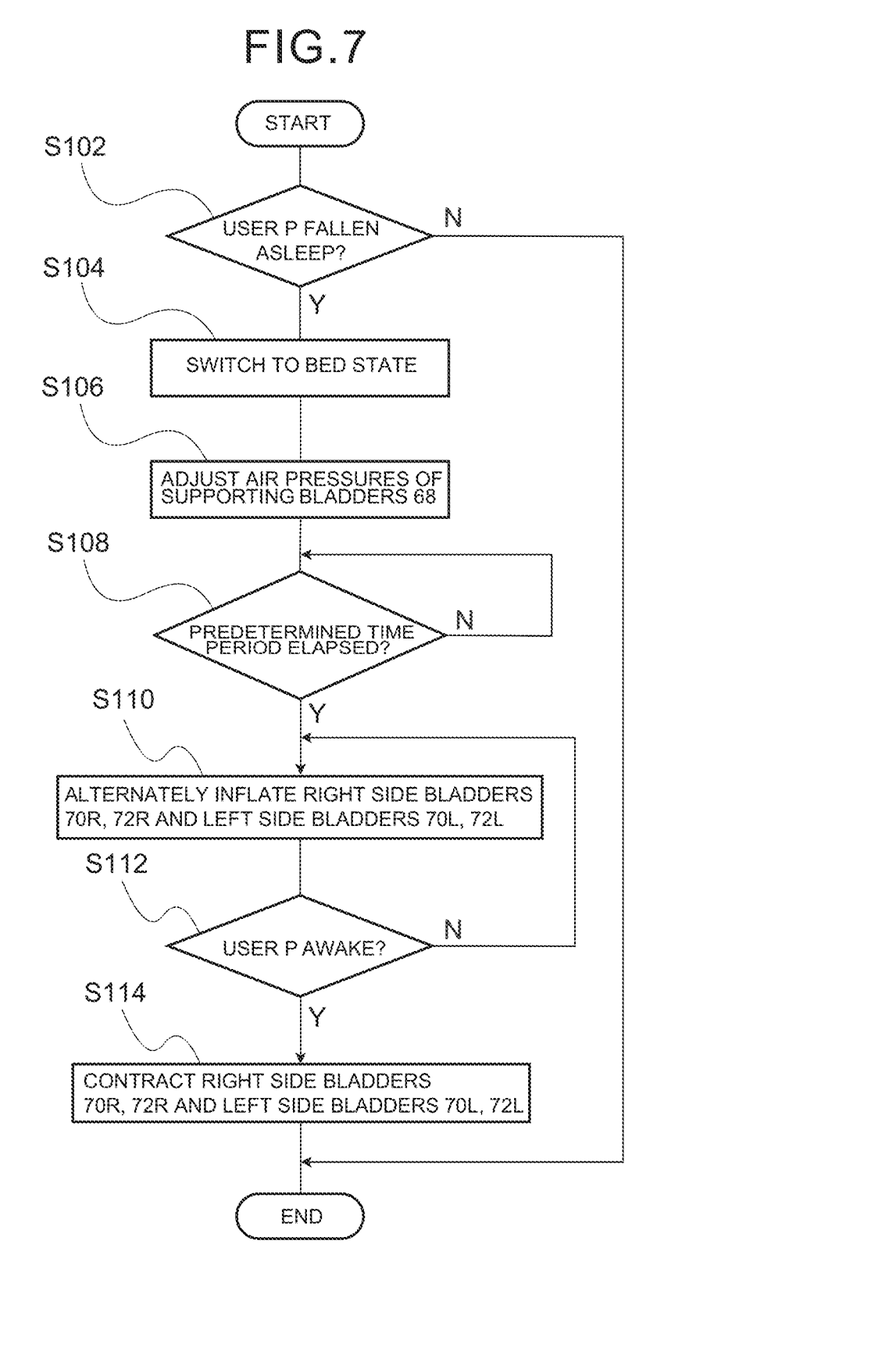
FIG. 7 is a flowchart illustrating an example of the flow of bladder controlling processing in the first embodiment.

As illustrated in FIG. 7, the sleep apparatus 10 is configured to include, as the functional configurations thereof, a receive section 70, an awakeness degree determination section 72, a seat transforming section 74, a supporting bladder control section 76, and a tilting bladder control section 78. Note that these respective functional configurations are realized by the CPU 44 reading-out a program that is stored in the ROM 46 or the storage 50, and executing the program.

The receive section 70 receives signals transmitted from the body pressure sensor 40 and the in-cabin camera 54 and the like. The awakeness degree determination section 72 determines the awakeness degree of the user P. Concretely, the awakeness degree determination section 72 determines whether or not the user P has fallen asleep, on the basis of information received from the body pressure sensor 40 and the in-cabin camera 54. For example, the awakeness degree determination section 72 may determine, from the signals received from the in-cabin camera 54 that the user P has fallen asleep in a case in which a state in which the user P has their eyes closed continues for a predetermined time period or more. Or, the awakeness degree determination section 72 may acquire time-series data of fluctuations in the heartbeat from the signals received from the body pressure sensor 40, and, on the basis of this time-series data of fluctuations in the heartbeat, may determine that the user P is not sleepy if there is a state in which sympathetic nerve activity is active and parasympathetic nerve activity is suppressed. Conversely, if there is a state in which sympathetic nerve activity is suppressed and the heartrate has fallen, the awakeness degree determination section 72 may determine that the user P is in a sleeping state. In the present embodiment, whether or not the user has fallen asleep is determined on the basis of both image data of the face of the user P that is acquired by the in-cabin camera 54, and heartbeat data of the user P that is acquired by the body pressure sensor 40.

In a case in which the awakeness degree determination section 72 determines that the user P has fallen asleep, the seat transforming section 74 transforms the mat main body portion 16 that is in the seat state, and switches it over to the bed state. Concretely, the seat transforming section 74 operates the upper side supporting portion rotation mechanism 56, the lower side supporting portion rotation mechanism 58 and the central supporting portion lifting mechanism 62 that are illustrated in FIG. 5, and makes the supporting surface of the upper side supporting portion 20 and the supporting surface of the lower side supporting portion 22 be in the same plane as the supporting surface of the central supporting portion 18. Further, the seat transforming section 74 operates the central supporting portion lifting mechanism 62, and lowers the central supporting portion 18. At this time, the seat transforming section 74 rotates the upper side supporting portion 20 and the lower side supporting portion 22 at a speed of an extent such that the user P does not wake up, and lowers the central supporting portion 18 at a speed of an extent such that the user P does not wake up. Moreover, due to the seat transforming section 74 operating the armrest movement mechanisms 60, the armrests 34 are lowered while being moved toward the seat rear side, in conjunction with the rotation of the upper side supporting portion 20. In this way, the mat main body portion 16 is switched-over from the seat state of FIG. 1 to the bed state of FIG. 2.

Figure 6:
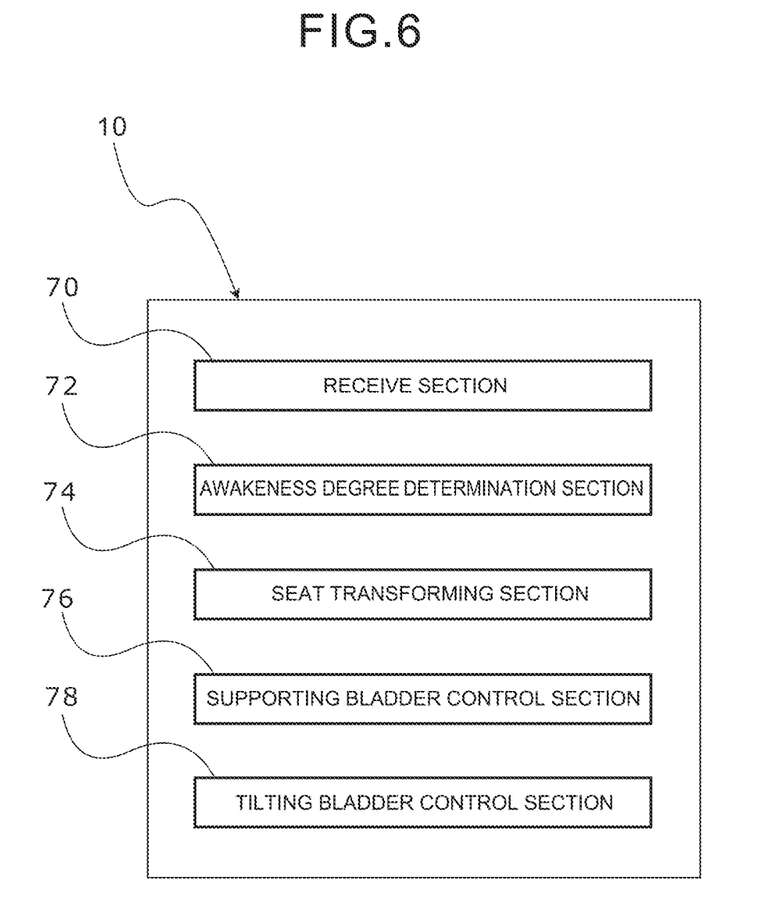
FIG. 6 is a block drawing illustrating functional configuration of the sleep apparatus relating to the first embodiment.

The supporting bladder control section 76 illustrated in FIG. 6 adjusts the air pressures of the supporting bladders 68 such that the air pressures of the supporting bladders 68 at the central supporting portion 18 are higher in the bed state than in the seat state. Concretely, due to the supporting bladder control section 76 controlling the amount of air that is supplied from the first air supply portion 64 illustrated in FIG. 5 to the supporting bladders 68, the supporting bladder control section 76 makes the air pressures of the supporting bladders 68 at the central supporting portion 18 high at the time when the main body portion 16 switches-over to the bed state. In the present embodiment, the air pressures of the supporting bladders 68 of the central supporting portion 18 that is in the seat state are set to be lower than those of the supporting bladders 68 that are disposed at the other portions. Further, at the time when the mat main body portion 16 switches-over to the bed state, the supporting bladder control section 76 adjusts the supporting bladders 68 at the central supporting portion 18 so as to become air pressures that are equivalent to those of the supporting bladders 68 that are disposed at other portions.

The tilting bladder control section 78 that is illustrated in FIG. 6 periodically tilts the body of the user P to the left and the right by controlling the second air supply portion 66 and alternately raising the right side supporting portion 16R and the left side supporting portion 16L. Concretely, in the state immediately after the mat main body portion 16 has switched-over to the bed state, the tilting bladder control section 78 does not supply air to any of the right side bladder 70R, the right side bladder 72R, the left side bladder 70L and the left side bladder 72L, as illustrated in FIG. 4A.

Figure 4A:
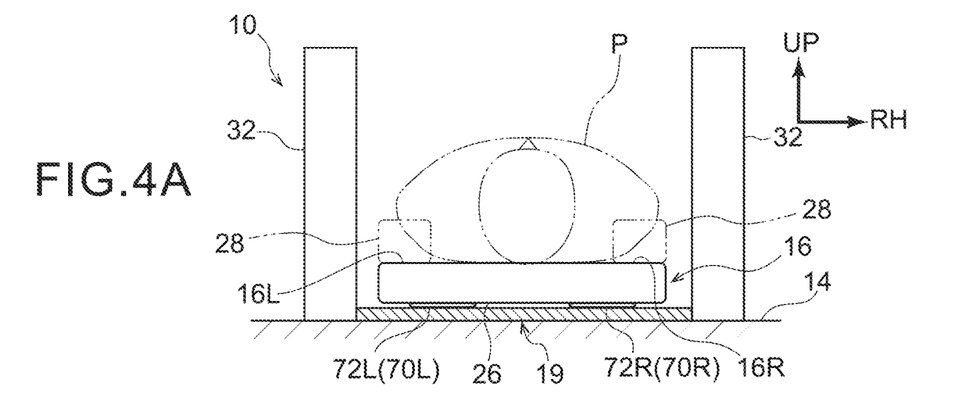
FIG. 4A is a drawing in which a state, in which a mat main body portion of the sleep apparatus relating to the first embodiment is in a horizontal state, is seen from a seat rear side.
Figure 4B:
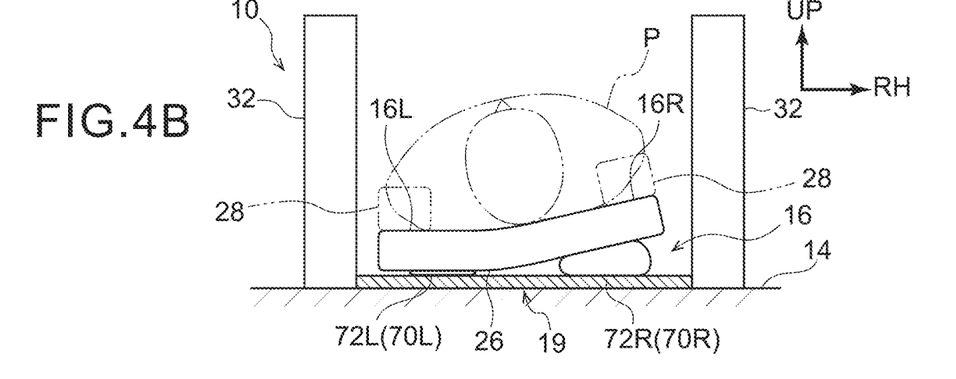
FIG. 4B is a drawing in which a state, in which the mat main body portion of the sleep apparatus relating to the first embodiment is tilted toward the left side, is seen from the seat rear side.

After a predetermined time has elapsed from the state of FIG. 4A, the tilting bladder control section 78 starts the supplying of air from the second air supply portion 66 to the right side bladder 70R and the right side bladder 72R. As illustrated in FIG. 4B, the tilting bladder control section 78 supplies air from the second air supply portion 66 until the right side bladder 70R and the right side bladder 72R become a predetermined air pressure, and thereafter, maintains the air pressures constant for a predetermined time period. At this time, as seen from the seat front-rear direction, there is a state in which the right side supporting portion 16R is tilted, and the body of the user P is tilted toward the left side.

Figure 4C:
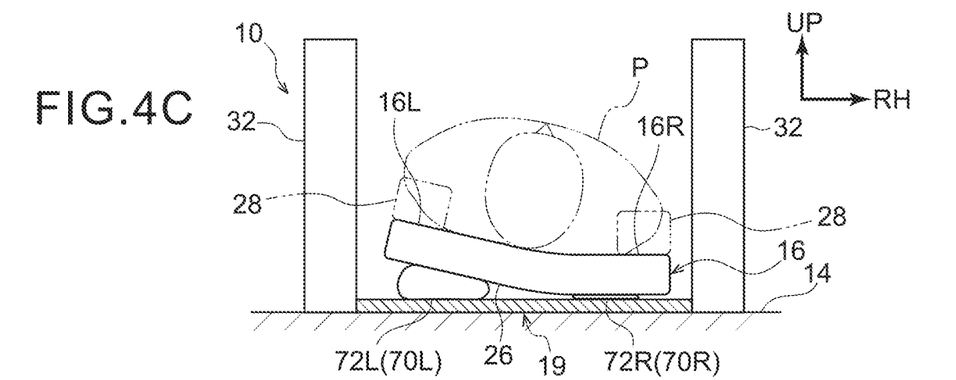
FIG. 4C is a drawing in which a state, in which the mat main body portion of the sleep apparatus relating to the first embodiment is tilted toward the right side, is seen from the seat rear side.

Next, from the state of FIG. 4B, the tilting bladder 78 control section stops the supply of air to the right side bladder 70R and the right side bladder 72R, and starts the supply of air to the left side bladder 70L and the left side bladder 72L. Due thereto, the right side bladder 70R and the right side bladder 72R contract, and, on the other hand, the left side bladder 70L and the left side bladder 72L inflate, and there becomes the state of FIG. 4C. Then, the tilting bladder control section 78 maintains the air pressures constant during a predetermined time period in the state of FIG. 4C. At this time, there becomes a state in which, as seen from the seat front-rear direction, the left side supporting portion 16L is tilted, and the body of the user P is tilted toward the right side. Then, as an example, the tilting bladder control section 78 of the present embodiment controls the second air supply portion 66 so as to alternately switch between the state of FIG. 4B and the state of FIG. 4C at a cycle of around 60 minutes.

Operation of the present embodiment is described next.

An example of the bladder controlling processing is described by using the flowchart illustrated in FIG. 7. This bladder control pressing is executed due to the CPU 44 reading-out a program from the ROM 46 or the storage 50, and expanding the program in the RAM 48 and executing the program.

As illustrated in FIG. 7, in step S102, the CPU 44 determines whether or not the user P has fallen asleep. Concretely, the CPU 44, by the function of the awakeness degree determination section 72 and on the basis of data acquired from the body pressure sensor 40 and the in-cabin camera 54, determines whether or not the user P has fallen asleep. Then, if it is determined that the user P has fallen asleep, the CPU 44 moves on to the processing of step S104. On the other hand, if it is determined that the user P has not fallen asleep, the CPU 44 ends the bladder controlling processing.

In step S104, the CPU 44 switches the mat main body portion 16 over from the seat state to the bed state. Concretely, by the function of the seat transforming section 74, the CPU 44 operates the upper side supporting portion rotation mechanism 56, the lower side supporting portion rotation mechanism 58, the central supporting portion lifting mechanism 62, and the armrest movement mechanisms 60, and switches the mat main body portion 16 to the bed state such that the sleep of the user P is not disturbed.

Next, in step S106, the CPU 44 adjusts the air pressures of the supporting bladders 68. Concretely, by the function of the supporting bladder control section 76, the CPU 44 increases the air pressures of the supporting bladders 68 at the central supporting portion 18, and makes the air pressures equal to the air pressures of the supporting bladders 68 at the other portions.

Then, in step S108, the CPU 44 determines whether or not a predetermined time period has elapsed from the switch-over to the bed state. If a predetermined time period has elapsed from the switch-over to the bed state, the CPU 44 moves on to the processing of step S110. Further, if a predetermined time period has not elapsed from the switch-over to the bed state, the CPU 44 repeats the processing of step S108 until the predetermined time period elapses.

In step S110, the CPU 44 alternately inflates the right side bladder 70R and the right side bladder 72R, and the left side bladder 70L and the left side bladder 72L. Concretely, by the function of the tilting bladder control section 78, the CPU 44 inflates the right side bladder 70R and the right side bladder 72R, and switches the mat main body portion 16 over to the state of FIG. 4B. Thereafter, the CPU 44 contracts the right side bladder 70R and the right side bladder 72R, and inflates the left side bladder 70L and the left side bladder 72L, and switches-over to the state of FIG. 4C. In this way, by alternately switching between the state of FIG. 4B and the state of FIG. 4C in a cycle of a predetermined time period, the CPU 44 periodically tilts the body of the user to the left and the right. Note that, from the state of FIG. 4A, the left side bladder 70L and the left side bladder 72L may first be expanded.

In step S112, the CPU 44 determines whether or not the user P is awake. Concretely, by the function of the awakeness degree determination section 72 and on the basis of the data acquired from the body pressure sensor 40 and the in-cabin camera 54, the CPU 44 determines whether or not the user P is awake. If the CPU 44 determines that the user P is awake, the CPU 44 moves on to the processing of step S114. On the other hand, if the CPU 44 determines that the user P is not awake, i.e., determines that the sleeping state of the user P is continuing, the CPU 44 continues the processing of step S110. Note that the processing of step S112 may be carried out at the point in time when one cycle of the processing of step S110 ends. Further, the awakeness degree of the user P may be monitored during the processing of step S110.

In step S114, the CPU 44 contracts the right side bladder 70R, the right side bladder 72R, the left side bladder 70L and the left side bladder 72L. Therefore, the mat main body portion 16 is switched-over to the state of FIG. 4A. Then, the CPU 44 ends the bladder controlling processing.

As described above, at the sleep apparatus 10 of the present embodiment, the body of the user P is tilted left and right periodically due to the right side supporting portion 16R and the left side supporting portion 16L being raised-up alternately. By periodically tilting the body of the user P left and right in this way, the region to which body pressure is applied may be changed periodically.

By the way, it is known that, while a person is sleeping, the person rolls over in their sleep several tens of times for the purpose of promoting blood circulation and the like. Here, in the sleep apparatus 10 relating to the present embodiment, circulation of blood is promoted due to the region, to which body pressure is applied, of the user P being changed periodically, and therefore, the sleeping state may be maintained favorable without the user P rolling-over. As a result, the sleeping state may be maintained favorable even in a case in which the sleeping space is of a narrow width. For example, in a case in which the sleep apparatus 10 is installed within the passenger cabin of the vehicle 12, because there are limits on the size of the sleep apparatus 10, the need to narrow the width of the mat main body portion 16 may arise. However, even in such a case, the sleeping state may be maintained favorable.

In particular, in the present embodiment, the right side supporting portion 16R and the left side supporting portion 16L may be raised alternately due to air being supplied from the second air supply portion 66 to the right side bladder 70R, the right side bladder 72R, the left side bladder 70L and the left side bladder 72L. Namely, the body of the user P may be tilted left and right by a simple structure.

Figure 2:
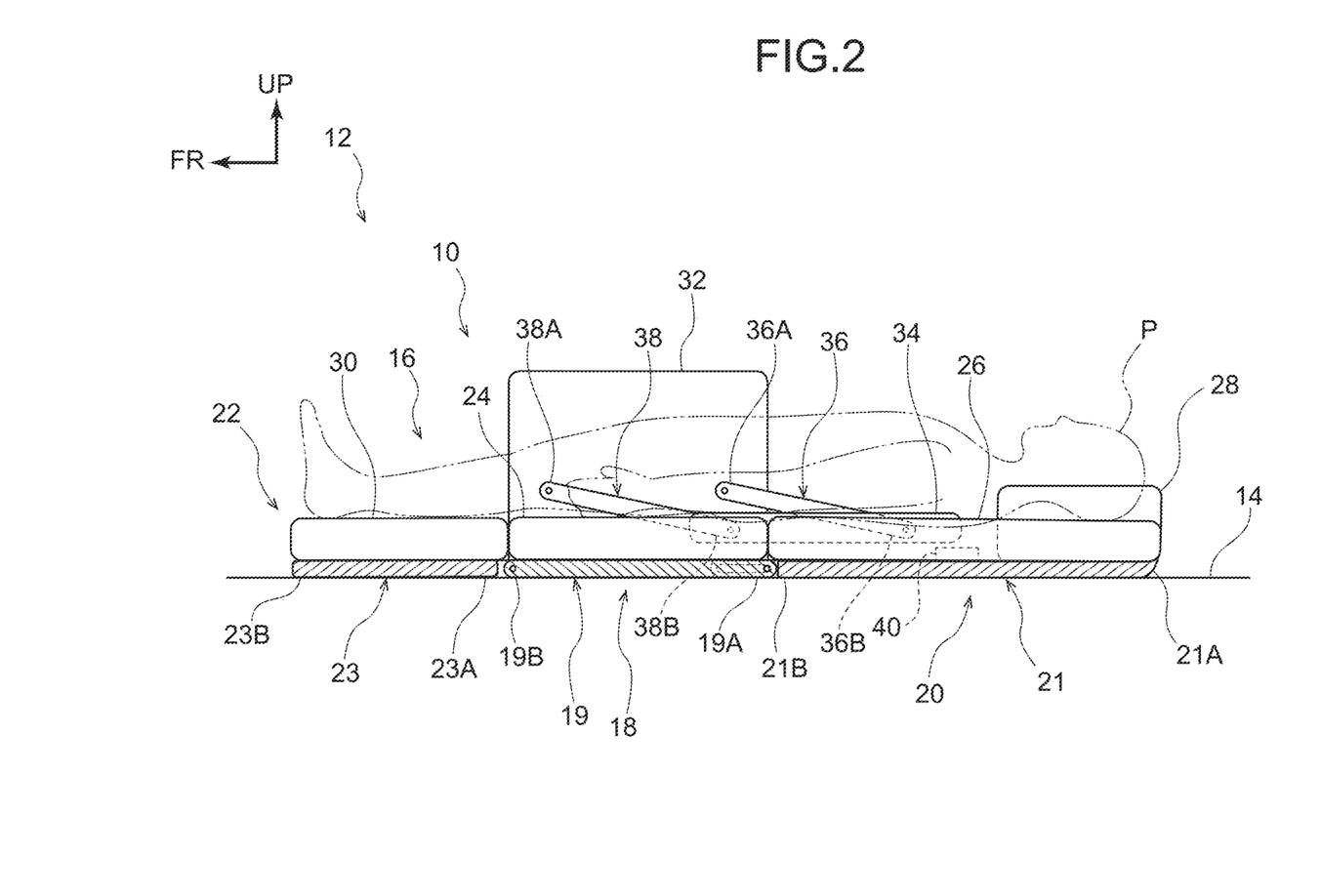
FIG. 2 is a schematic side sectional view in which the sleep apparatus relating to the first embodiment is seen from the seat width direction, and is a drawing illustrating a bed state.

Further, in the present embodiment, the mat main body portion 16 is structured so as to be able to switch-over alternately between the seat state and the bed state. Therefore, in a case in which the user P is sitting on the mat main body portion 16 that is in the seat state as illustrated in FIG. 1, the buttocks and thigh regions of the user P are supported from the lower side by the central supporting portion 18, and the back region and head portion are supported from the rear side by the upper side supporting portion 20, and the leg portions are supported from the rear side by the lower side supporting portion 22. Then, by switching the mat main body portion 16 over from this seat state to the bed state, as illustrated in FIG. 2, the user may assume a recumbent posture without separating from the mat main body. In this way, the sleep apparatus 10 may be used both in a posture in which the user P is seated and a posture in which the user is recumbent.

Moreover, in the present embodiment, the plural supporting bladders 68 are disposed along the seat front-rear direction at the mat main body portion 16. The respective supporting bladders 68 are structured such that the air pressures of the interiors thereof may be changed. Due thereto, the hardness of the mat main body portion 16 may be adjusted in accordance with the posture of the user P. Further, the air pressures of the supporting bladders 68 are adjusted by the supporting bladder control section 76 so that the air pressures of the supporting bladders 68 at the central supporting portion 18 are higher in the bed state than in the seat state. Due thereto, in the bed state, the air pressures of the supporting bladders 68 at the central supporting portion 18 may be raised, and it may be made easy to tilt the body of the user P to the left and the right, while, in the seat state, the air pressures of the supporting bladders 68 at the central supporting portion 18 may be lowered, and the buttocks and thigh regions of the user P may be supported so as to be enfolded. As a result, the comfort of the user P may be ensured in both the seat state and the bed state.

Still further, at the sleep apparatus 10 of the present embodiment, when the user P falls asleep, the mat main body 16 is switched-over from the seat state to the bed state. Due thereto, when the user P falls asleep in a state of sitting on the mat main body portion 16 that is the seat state, the mat main body portion 16 may be switched-over to a posture in which it is easy to sleep.

Further, in the present embodiment, at the time when the mat main body portion 16 switches-over from the seat state to the bed state, the armrest movement mechanisms 60 lower the armrests 34 in conjunction with the rotation of the upper side supporting portion 20. Due thereto, even in a case in which the user P falls asleep in a state of being seated on the mat main body portion 16 that is in the seat state and with his/her arms resting on the armrests 34, the user may be switched-over to a recumbent posture without sleep being disturbed. Namely, as compared with a structure in which the armrest movement mechanisms 60 are not provided, the sleep of the user P being disturbed at the time when the user P switches-over to the recumbent posture may be suppressed.

Figure 8A:
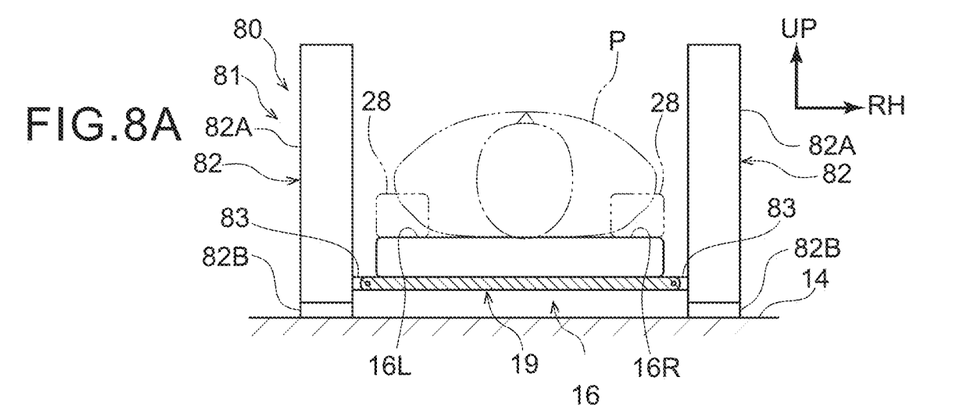
FIG. 8A is a drawing in which a state, in which the mat main body portion of an sleep apparatus relating to a second embodiment is in a horizontal state, is seen from the seat rear side.
Figure 8B:
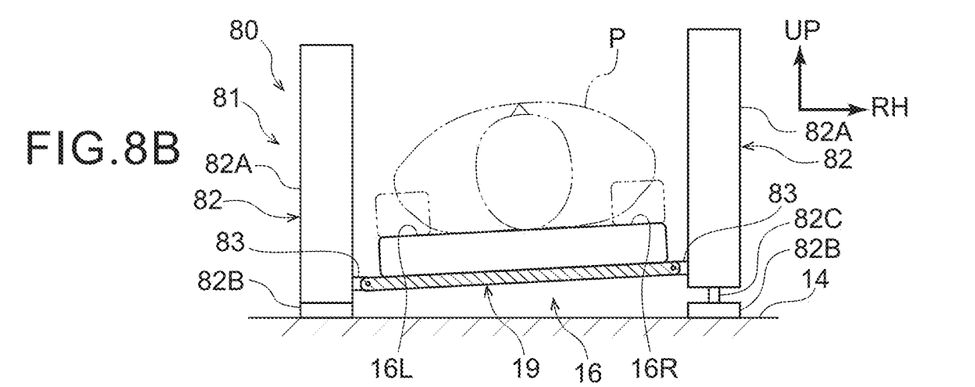
FIG. 8B is a drawing in which a state, in which the mat main body portion of the sleep apparatus relating to the second embodiment is tilted toward the left side, is seen from the seat rear side.
Figure 8C:
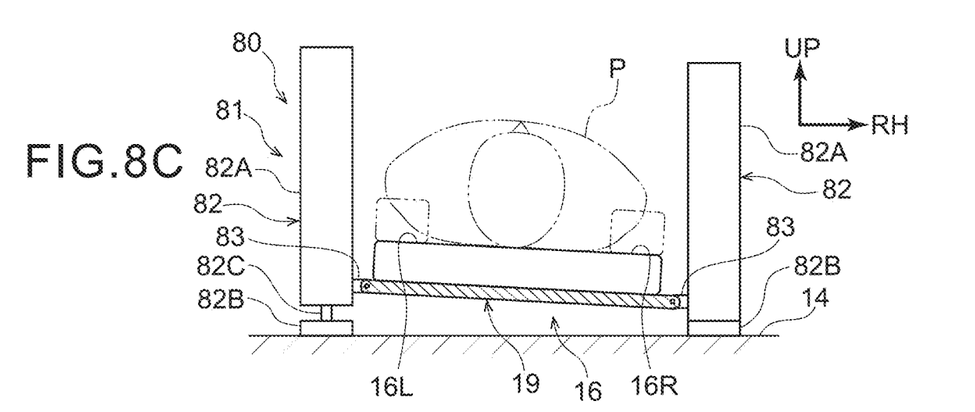
FIG. 8C is a drawing in which a state, in which the mat main body portion of the sleep apparatus relating to the second embodiment is tilted toward the right side, is seen from the seat rear side.

An apparatus 80 for sleeping relating to a second embodiment of the present disclosure is described next with reference to FIG. 8A through FIG. 8C. Note that structures that are similar to those of the first embodiment are denoted by the same reference numerals, and description thereof is omitted as appropriate.

The apparatus 80 for sleeping of the present embodiment differs from the first embodiment with regard to the points that the apparatus 80 for sleeping has a tilting device 81, and the entire mat main body portion 16 is tilted left and right by this tilting device 81. The tilting device 81 is structured to include side frames 82. The side frames 82 stand upright at the seat width direction both sides of the central supporting frame 19, and each are structured to include a base portion 82B, a moving portion 82A, and shaft portions 82C.

The base portion 82B is formed in the shape of a rectangular plate whose length direction is the seat front-rear direction, and is fixed to the floor panel 14. The moving portion 82A is provided at the upper portion of the base portion 82B.

The moving portion 82A is formed in a rectangular shape that has substantially the same outer shape as the base portion 82B as seen in a plan view, and is formed such that the length thereof in the seat vertical direction is longer than that of the base portion 82B. Further, a connecting piece 83 projects-out toward the mat main body portion 16 side from the lower portion of the moving portion 82A that is at the right side. The right side end portion of the central supporting frame 19 is connected to this connecting piece 83 so as to rotate freely. Moreover, the connecting piece 83 projects-out toward the mat main body portion 16 side from the lower portion of the moving portion 82A that is at the left side. The left side end portion of the central supporting frame 19 is connected to this connecting piece 83 so as to rotate freely.

Here, unillustrated insertion holes are formed in the lower end surface of the moving portion 82A, and the shaft portions 82C are inserted in these insertion holes. The shaft portions 82C are formed in substantially cylindrical shapes, and extend toward the seat upper side from the base portion 82B, and a plurality thereof are provided along the seat front-rear direction. In this way, the moving portion 82A is structured so as to be able to move in the seat vertical direction along the shaft portions 82C.

An unillustrated moving mechanism is provided at the interior of the moving portion 82A. The moving portion 82A is raised due to the moving portion 82A being pushed-up with respect to the shaft portions 82C due to this moving mechanism operating. Further, in the present embodiment, the entire mat main body portion 16 is tilted left and right by the left and right moving portions 82A being raised alternately. As a result, the right side supporting portion 16R and the left side supporting portion 16L are raised-up alternately, and the body of the user P is periodically tilted left and right.

Operation of the present embodiment is described next.

In the present embodiment, the mat main body portion 16 may be tilted more rapidly, as compared with a structure in which the right side supporting portion 16R and the left side supporting portion 16L are raised alternately due to bladders being inflated as in the first embodiment. As a result, in a case in which it is predicted that the user P will turn over in their sleep toward the left side, due to the moving portion 82A at the right side being raised, the action of the user P turning-over in their sleep may be followed. Other operations are the same as in the first embodiment.

A test on sleeping efficiency was carried out in order to confirm the effects of the present disclosure. Two men and two women in their 40's were the subjects. A wristwatch-type acceleration sensor was attached to each subject. The time period in which motion was sensed by the acceleration sensor was measured as the awake time period, and the time period in which motion was hardly sensed or not at all sensed was measured as the asleep time period.

Measurement was carried out for five days while changing the conditions of the bed for each subject. The conditions of the bed were as follows. Note that, on the fourth and fifth days, a narrow bed at which the width of the mat main body portion 16 was 550 mm was used, in the same way as on the third day.

First day: a general bed

Second day: a bed whose reclining angle could be adjusted automatically in accordance with the awakeness degree of the user Third day: a narrow bed at which the width of the mat main body portion was 550 mm Fourth day: the tilting angle at the sleep apparatus 10 of the first embodiment was 8°

Fifth day: the tilting angle at the sleep apparatus 10 of the first embodiment was 16°

Figure 9:
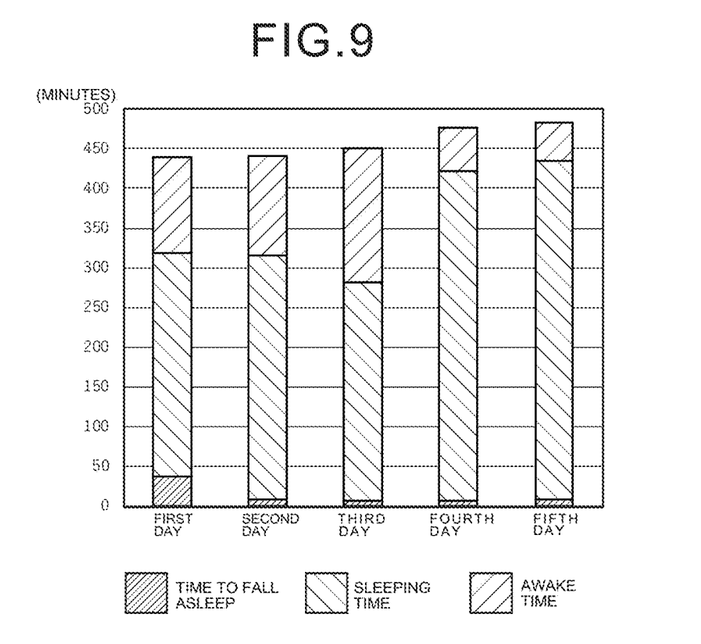
FIG. 9 is a graph illustrating the relationships between sleeping conditions and sleeping times for subject A.

The results of the test on the male in his 40's who was the first subject are illustrated in FIG. 9. As can be seen from the graph of FIG. 9, the asleep time period on the narrow bed was short as compared with on a general bed. Further, by using the sleep apparatus 10 of the first embodiment, even though the bed was narrow, the asleep time period was long as compared with on a general bed. Namely, it was confirmed that the quality of sleep was improved regardless of the fact that the width of the bed was narrow. Note that there was no great difference in the asleep time period in the case in which the tilting angle was 8° and in the case in which the tilting angle was 16°.

Figure 10:
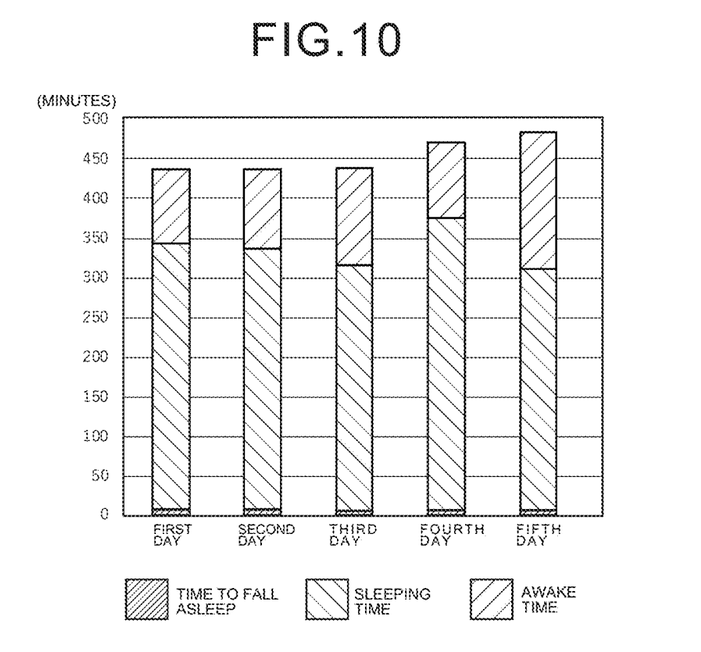
FIG. 10 is a graph illustrating the relationships between sleeping conditions and sleeping times for subject B.

The results of the test on the female in her 40's who was the second subject are illustrated in FIG. 10. As can be seen from the graph of FIG. 10, the asleep time period was longest in the case in which the tilting angle of the sleep apparatus 10 was 8°. Further, in the case in which the tilting angle of the sleep apparatus 10 was 16°, the asleep time period was shorter than in the case in which the tilting angle was 8°. It is assumed that the subject was awake because the tilting angle was made to be large.

Figure 11:
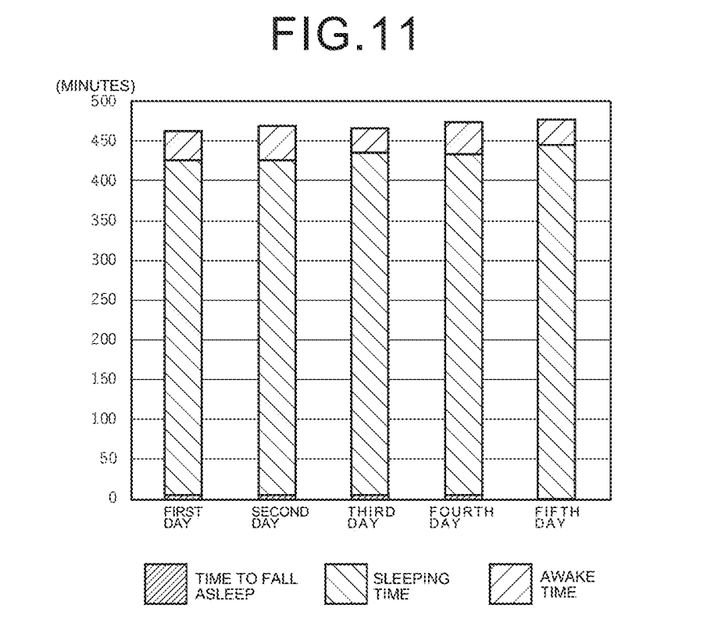
FIG. 11 is a graph illustrating the relationships between sleeping conditions and sleeping times for subject C.

The results of the test on the male in his 40's who was the third subject are illustrated in FIG. 11. As can be seen from the graph of FIG. 11, there were no great differences in the asleep time periods under all of the conditions. From this, it is assumed that, for a subject who tends to find it easy to fall asleep, the sleeping state may be maintained favorable under all conditions.

Figure 12:
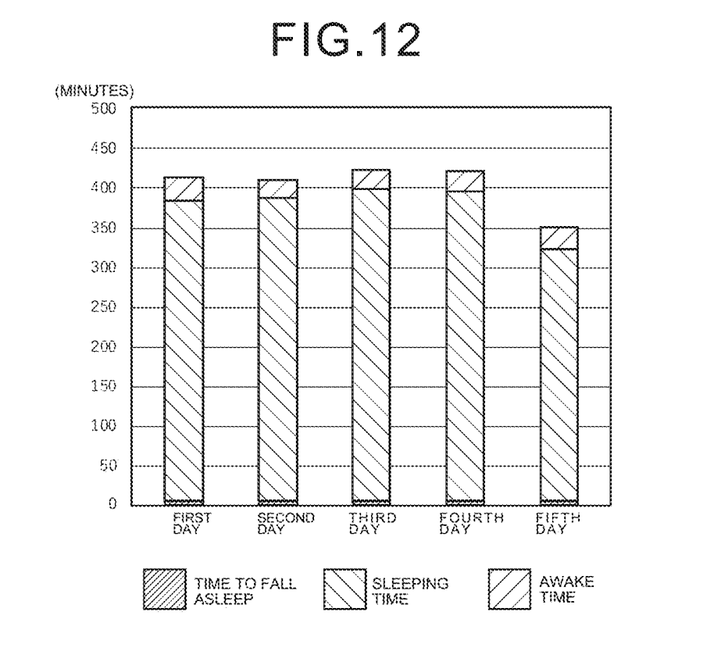
FIG. 12 is a graph illustrating the relationships between sleeping conditions and sleeping times for subject D.

The results of the test on the female in her 40's who was the fourth subject are illustrated in FIG. 12. As can be seen from FIG. 12, the asleep time period was shortest in the case in which the tilting angle of the sleep apparatus 10 was 16°, and there was no great difference in the asleep time periods under the other conditions. From this, it is assumed that this subject as well had the tendency to find it easy to fall asleep, but, that when the tilting angle was 16°, the subject experienced an uncomfortable feeling and was awake.

From the above test results, it was confirmed that, for all of the subjects, by setting the tilting angle of the sleep apparatus 10 to 8°, the sleeping state may be maintained favorable even on a narrow bed.

The apparatuses 10, 80 for sleeping relating to the first embodiment and the second embodiment have been described above. However, the present disclosure can, of course, be implemented in various ways within a scope that does not depart from the gist thereof. For example, the above-described embodiments are structured such that the right side supporting portion 16R and the left side supporting portion 16L are raised alternately in cycles of a predetermined time period. However, the present disclosure is not limited to this, and the right side supporting portion 16R and the left side supporting portion 16L may be raised alternately on the basis of other conditions.

Concretely, the right side supporting portion 16R and the left side supporting portion 16L may be raised alternately in a case in which the depth of sleep of the user P is deeper than a predetermined value. For example, control may be carried out such that the tilting mechanism is operated, and the right side supporting portion 16R and the left side supporting portion 16L are raised alternately, only at times of non-REM sleep in which sleep is deep. Or, the tilting mechanism may be operated in cases in which the depth of sleep is a 2 or a 3, which is a deep sleep, among the three levels of depth during non-REM sleep. In this case, it may be determined whether or not the depth of sleep of the user P who is sleeping has reached a depth of 3 in non-REM sleep, by providing a depth sensor that senses the depth of sleep of the user P. In this way, by operating the tilting mechanism when the user P is in a deep sleep, the body of the user P may be tilted left and right without the user P who is sleeping noticing. Note that a sensor that may sense brainwaves of the user P, or a sensor that may sense movement of the eyeballs of the user P, or the like may be used as the depth sensor. Eyeball movement is active during REM sleep, whereas the eyeballs hardly move at all during non-REM sleep, and therefore, a REM sleep state and a non-REM sleep state may be sensed.

Further, the above-described embodiments describe structures in which the mat main body portion 16 may switch-over from the seat state to the bed state, but the present disclosure is not limited to this. For example, an sleep apparatus that does not switch-over from the bed state may be used. In this case, the upper side supporting portion rotation mechanism 56, the lower side supporting portion rotation mechanism 58 and the central supporting portion lifting mechanism 62 that are illustrated in FIG. 5 are not needed. Further, because the main purpose of the bed is sleeping, the armrests 34 as well are unnecessary.

Moreover, although the above embodiment describes a structure in which the sleep apparatus 10 is installed in the vehicle 12, the present disclosure is not limited to the same, and, for example, the sleep apparatus 10 may be disposed in a living space such as in a home or the like, for example.

Still further, in the above-described first embodiment, a structure is described in which the two right side bladders 70R, 72R and the two left side bladders 70L, 72L are provided. However, the present disclosure is not limited to this. For example, there may be a structure in which three or more right side bladders and three or more left side bladders are provided. Further, the right side bladder 70R and the right side bladder 72R may be connected so as to form a single right side bladder, and the left side bladder 70L and the left side bladder 72L may be connected so as to form a single left side bladder.

What is claimed is:

1. A sleep apparatus, comprising:
    a mat main body portion configured to support a user in a supine state;
    a tilting mechanism including a right side support portion and a left side supporting portion, and configured to, at the mat main body portion, periodically tilt a body of the user left and right, by alternately raising the right side supporting portion including portions supporting a right-side hipbone and a right-side shoulder blade of the user, and the left side supporting portion including portions supporting a left-side hipbone and a left-side shoulder blade of the user; and
    a plurality of supporting airbags provided at the mat main body portion, wherein
    the mat main body portion includes an upper side supporting portion, a lower side supporting portion, and a central supporting portion between the upper and lower side supporting portions,
    the mat main body portion is configured to alternately switch between a seat state and a bed state,
    the supporting airbags are disposed along a direction heading from the upper side supporting portion toward the lower side supporting portion,
    internal air pressures of the supporting airbags are respectively adjustable, and
    the internal air pressures of the supporting airbags are adjusted to cause the internal air pressures of the supporting airbags at the central supporting portion to be higher in the bed state than in the seat state.

2. The sleep apparatus of claim 1, wherein
    the central supporting portion is configured to support buttocks and thigh regions of the user,
    the upper side supporting portion is rotatably connected to one end side of the central supporting portion and configured to support a back region and head portion of the user,
    the lower side supporting portion is rotatably connected to another end side of the central supporting portion and configured to support leg portions of the user, and
    the mat main body portion is configured to alternately switch between the seat state and the bed state, by the upper side supporting portion and the lower side supporting portion rotating with respect to the central supporting portion.

3. The sleep apparatus of claim 2, wherein a pair of left and right head portion restraining cushions are provided at the upper side supporting portion to allow the head portion of the user to be located therebetween.

4. The sleep apparatus of claim 2, further comprising:
    armrests that are provided at respective side portions of the mat main body portion, and are configured to support arms of the user in the seat state; and
    armrest movement mechanisms that, at a time of switching from the seat state to the bed state, are configured to lower the armrests in conjunction with rotation of the upper side supporting portion.

5. The sleep apparatus of claim 2, further comprising a wakefulness sensor configured to sense a degree of wakefulness of the user seated on the mat main body portion in the seat state,
    wherein, in response to the degree of wakefulness sensed by the wakefulness sensor being lower than a predetermined value, the mat main body portion is configured to be switched from the seat state to the bed state.

6. The sleep apparatus of claim 5, wherein the wakefulness sensor comprises a body pressure sensor that is provided at a position of the mat main body portion corresponding to the heart of the user, and that is configured to sense a heartbeat of the user.

7. The sleep apparatus of claim 1, further comprising a depth sensor configured to sense a depth of sleep of the user,
    wherein, in response to the depth of sleep sensed by the depth sensor being greater than a predetermined value in the bed state, the tilting mechanism is configured to alternately raise the right side supporting portion and the left side supporting portion.

8. The sleep apparatus of claim 1, wherein the sleep apparatus is disposed within a passenger cabin of a vehicle.

9. The sleep apparatus of claim 1, wherein the tilting mechanism comprises:
    tilting airbags that are provided at the right side supporting portion and the left side supporting portion, respectively; and
    an air supply portion configured to supply air to the tilting airbags.

10. The sleep apparatus of claim 1, wherein the tilting mechanism comprises a tilting device configured to tilt an entirety of the mat main body portion left and right.

11. The sleep apparatus of claim 1, wherein
    the supporting airbags at the central supporting portion are disposed adjacent to each other along a first direction defined by the direction heading from the upper side supporting portion toward the lower side supporting portion, and
    the left and right side support portions are disposed adjacent to each other in a second direction crossing the first direction.

12. The sleep apparatus of claim 11, wherein
    each of the supporting airbags at the central supporting portion extends across both the left and right side support portions as viewed in a third direction perpendicular to the first and second directions.

* * * * *